United States Patent [19]
DeSimone et al.

[11] Patent Number: 5,410,013
[45] Date of Patent: Apr. 25, 1995

[54] THIOPHENE-CONTAINING POLY(ARYLENE ETHER) SULFONES

[75] Inventors: Joseph M. DeSimone; Edward T. Samulski, both of Chapel Hill; Robert S. Archibald, Carrboro; Valeria V. Sheares, Clayton, all of N.C.

[73] Assignee: The University of North Carolina at Chapel Hill, Chapel Hill, N.C.

[21] Appl. No.: 252,385

[22] Filed: Jun. 1, 1994

Related U.S. Application Data

[63] Continuation of Ser. No. 99,731, Jul. 30, 1993, abandoned.

[51] Int. Cl.⁶ .......................... C08G 8/02; C08G 8/26; C08G 75/23

[52] U.S. Cl. .................... 528/171; 428/411.1; 528/125; 528/128; 528/174; 528/373; 528/377; 528/380

[58] Field of Search ............... 428/411.1; 528/125, 528/128, 171, 174, 373, 377, 380

[56] References Cited

U.S. PATENT DOCUMENTS

| | | | |
|---|---|---|---|
| 5,047,496 | 9/1991 | Eckel et al. | 528/171 |
| 5,266,677 | 11/1993 | Samulski et al. | 528/310 |
| 5,354,836 | 10/1994 | Samulski et al. | 528/125 |

Primary Examiner—John Kight, III
Assistant Examiner—Shelley A. Dodson
Attorney, Agent, or Firm—Bell, Seltzer, Park & Gibson

[57] ABSTRACT

Poly(arylene ether) sulfones that contain thiophene rings within the aromatic polymer backbone are disclosed, along with fibers, films, and other articles of manufacture formed therefrom.

23 Claims, 4 Drawing Sheets

THIOPHENE-CONTAINING POLY(ARYLENE ETHER) SULFONES

This is a Continuation of application Ser. No. 08/099,731, filed on 30 Jul. 1993, now abandoned.

FIELD OF THE INVENTION

The invention relates generally to poly(arylene ether) sulfone polymers, and relates more specifically to poly(arylene ether) sulfone polymers containing thiophene rings.

BACKGROUND OF THE INVENTION

Poly(arylene ether sulfone)s (PAES) are recognized as important high performance engineering thermoplastics. Commercially available materials include those sold under the trademarks Udel (shown as Formula I)

and Victrex (shown as Formula II).

PAES materials are generally regarded as having high tensile and flexural strength and excellent oxidative, thermal, and hydrolytic stability. PAES is used for a variety of component parts, such as those employed for ultrafiltration, and also can be used as matrix for composites, coatings, and adhesives.

An exemplary polymerization method for producing PAES is disclosed in Johnson et al., *J. Polymer Sci. Pt. A.*, 5:2375 (1967), which describes step growth polymerization of 4,4'-dichlorodiphenylsulfone and various biphenols using aprotic solvents such as DMSO and potassium hydroxide. McGrath et al., Polymer, 25:1827 (1984), notes that this polymerization proceeds with excess potassium hydroxide and dimethylacetamide as a solvent.

Thiophene is five-membered aromatic ring (Formula III)

that has been introduced into the polymer backbone of commercially known polymers such as poly(ethylene terephthalate), poly(ether ether ketone) and poly(a-rimid). Because they include only six-membered aromatic ring structures, the non-thiophene containing analogs of these compounds are linked so that the bond angles about the individual aromatic rings of the backbone are either 120 or 180 degrees. The introduction of the five-membered thiophene ring into the polymer backbone causes the backbone to include additionally bond angles of 148 degrees. This substitution in the polymer backbone modifies the crystalline structure of the polymer and thereby provides the polymer with, inter alia, different mechanical, thermal, chemical, and crystalline properties.

In view of the foregoing, it is an object of the present invention to provide polymer alternatives to PAES which have different physical, chemical, and processing characteristics to increase the range of applications for these types of materials.

SUMMARY OF THE INVENTION

This and other objects are satisfied by the present invention, which includes a poly(arylene ether sulfone) comprising repeating units of Formula IV wherein R is an aromatic moiety having at least one aromatic ring. Preferably, R is a moiety of Formula V wherein A is an aromatic group having at least one aromatic ring, and B is an aromatic group having at least one aromatic ring. Polymers of the present inventors can be used to form molded articles, films, fibers, composite matrices, and the like.

DETAILED DESCRIPTION OF THE INVENTION

The present invention regards the introduction of the thiophene moiety into the backbone of poly(arylene ether)sulfones. Thiophene is a highly aromatic organic moiety, and thus is an attractive choice for inclusion into high temperature polymers, as these polymers require thermally and chemically stable moieties to withstand the polymerization, processing, and end use conditions to which the polymer is exposed. The substitution of a thiophene moiety for a 1,4 linked phenyl group into a polymer backbone introduces an angle or "kink" of 148° into the otherwise linear (180°) polymer chain; this angle differs from that produced by the inclusion of a 1,3-linked phenyl group in the chain, which introduces a 120° kink into the chain. The presence of the 148° kink in the backbone influences several physical properties of the polymer, including toughness, tensile strength, and crystallization percentage and rate.

Inclusion of thiophene into an aromatic polymer chain backbone also provides a functionality, namely a sulfur atom, which influences the polymer's chemical properties and can favorably influence the ability of the polymer chain to interact with other substances within a mixture. For example, the presence of the sulfur-containing heterocycle can affect the dielectric properties of a polymer, its optical properties, and its permeability to different gasses, each of which are properties that end-users of a polymer may find attractive. In addition, the inclusion of thiophene can improve the compatibility of a polymer with other polymer types in a blend or alloy, the adhesion of the polymer to organic or inorganic substrates, such as in a coating or in a composite matrix, and the polymer's solubility in various solvents.

As a first aspect, the present invention includes a poly(arylene ether) sulfone comprising repeating units of Formula IV, (IV)

wherein R is an aromatic moiety as described above. The aromatic moiety R can be any aromatic moiety that includes at least one aromatic ring. The aromatic ring may be entirely composed of carbon atoms or may be heterocyclic. Multiple rings can be directly covalently linked, as in biphenyl, can be linked by an alkyl group, as in diphenyl isopropane, or can be linked by a different functional group, such as an ether, a sulfone, or a ketone. The aromatic rings may be unsubstituted or substituted, as may any linkage which bonds multiple aromatic rings, but the substituents should include only those which will not interfere with the polymerization process, such as alkyl groups, alkoxy groups, and phenyl and other aromatic groups. Exemplary aromatic groups include phenyl, biphenyl, diphenylisopropane, naphthalene, anthracene, phenanthrene, naphthacene, pentacene, pyridines, thiophenes, and other aromatic groups, such as the aromatic groups of the diphenols listed in Vriesema, U.S. Pat. No. 4,876,327, the subject matter of which is incorporated herein by reference in its entirety. Preferably, the sulfone and ether functionalities link to the aromatic groups at positions that are 180 degrees across the aromatic ring from one another (e.g., in the 1 and 4 positions of a phenyl group, or the 4 and 4' positions of a biphenyl group) to provide a linear portion to the polymer chain.

It is preferred that R in Formula IV comprises an arylene ether of Formula V, (V)

wherein A and B are aromatic groups as described above. The aromatic rings of A and B can be entirely composed of hydrocarbon or can be heterocyclic. Any of the aromatic rings of A and B can be unsubstituted or substituted; the substituents should be chosen so as not to interfere with the polymerization of the polymer. Suitable substituents include alkyl groups, alkoxy groups, and substituted or unsubstituted phenyl groups.

In particular, A is preferably thiophene or phenyl. If A is thiophene, B is preferably selected from the group consisting of phenyl, biphenyl, diphenylisopropyl, diphenyl ketone, diphenyl sulfone, and diphenyl ether. If A is phenyl, B is preferably a moiety selected from the group consisting of phenyl, biphenyl, diphenyl isopropanyl, diphenyl ketone, diphenyl sulfone, 4-phenyl-2-sulfonylthiophene, and diphenyl ether.

The poly(arylene ether)sulfones of the present invention can comprise a copolymer which includes aromatic sulfone units or ether units which do not include a thiophene ring. The substitution of these units can alter the physical properties of the polymer by increasing the linearity of the polymer backbone and by modifying the functional groups available for interaction with other materials in a mixture. Such sulfone units are typically linked at each end by an ether linkage to the oxygen atom attached to the thiophene moiety of Formula IV. Exemplary aromatic sulfone units suitable for inclusion in a copolymer include diphenyl sulfone, di-biphenyl sulfone, phenyl-biphenyl sulfone, 1,4-bis(phenyl sulfonyl) benzene, and 1,3-bis(phenyl sulfonyl) benzene. Exemplary aromatic ether units include diphenyl ether, di-biphenyl ether, phenyl-biphenyl ether, 1,3-bis(phenylsulfonyl) benzene, and 1,4-bis(phenylsulfonyl) benzene.

The synthesis of the poly(arylene ether)sulfones of the present invention can be carried out by known polymerization methods for poly(arylene ether)sulfones. Exemplary is a nucleophilic substitution reaction, wherein one monomer comprising a dihalide form of an aromatic thiophene sulfone defined by the thiophene moiety and aromatic group A of Formula II is polymerized with a diphenol having the aromatic structure of monomer B in Formula II. Generally the monomers are added in stoichiometric ratio in a polar, aprotic solvent, such as dimethylacetamide, then heated. The phenolic hydrogens of monomer B and the halogens of the aromatic sulfone thiophene monomer are displaced, thereby permitting the formation of an ether linkage between the monomers. This reaction can be carried out in the presence of a weak base, such as potassium carbonate, and an azeotroping agent, such as toluene. Exemplary dihalogenated aromatic thiophene sulfone monomers include 2-chloro-5-(4'-chlorophenylsulfonyl)thiophene, 2-chloro-5-(4'-fluorophenylsulfonyl)thiophene, 2-chloro-5-(4'-chlorobiphenylsulfonyl)thiophene, 2-chloro-5-(4'-fluorobiphenylsulfonyl)thiophene, and Bis-(5-chloro-2-thiophenidyl)sulfone. Exemplary aromatic diphenols include 4-hydroxyphenol (hydroquinone), biphenol, 4,4'-isopropanidyl diphenol (Bisphenol A), bis-(4-hydroxyphenyl)ketone, bis-(4-hydroxyphenyl)sulfone, bis-(4-hydroxyphenyl)ether, and 2-hydroxy-5-([4'-hydroxyphenyl]sulfonyl)thiophene.

The polymers of the present invention can also be produced by polymerizing a self-polymerizing aromatic thiophene sulfone, such as phenylthiophene sulfone, having a halogen atom on the thiophene moiety and a hydroxyl group on a separate aromatic ring. Typically the monomer is reacted in a polar, aprotic solvent, such as dimethylacetamide, then heated. The hydrogen atom of the hydroxyl group attached to the hydroxyl group and the halogen of the aromatic sulfone thiophene monomer B are removed during the reaction, thereby permitting the formation of an ether linkage between the monomer units. This reaction can be carried out in the presence of a weak base, such as potassium carbonate, and an azeotroping agent, such as toluene. Exemplary self-polymerizing monomers include 2-chloro-5-([4'-hydroxyphenyl]sulfonyl)thiophene, 2-chloro-5-([4'-hydroxybiphenyl]sulfonyl)thiophene, and 2-chloro-5-[4'-hydroxyphenylphenylisopropanyl]sulfonyl thiophene.

The polymer can take a number of useful forms. It can be spun or otherwise manufactured into high-strength fibers. It can also be extruded, solvent cast, or otherwise formed into high-strength films, membranes, and sheets. It can be ground into a filled or unfilled resin to be subsequently formed into molded articles of a desired configuration. Because of the functionality provided by the sulfur atom of the thiophene group, the polymer has enhanced adhesive properties, and thus can be used as a coating on a foreign substrate, or as the matrix component of a composite material containing inorganic or organic fillers such as carbon fibers, glass fibers, glass beads, mineral fibers, talc, and the like.

The present invention is described in greater detail in the following examples, which are not intended to be limiting, but instead are provided for more complete understanding of the invention. As used herein, "mL" means milliliters, "g" means grams, "° C" means degrees Centigrade, "M" means molar concentration, "$T_m$" means melting point, "$M_n$" means molecular weight, and "$T_g$" means glass transition temperature.

EXAMPLE 1

Reagents

The materials used in the following examples were acquired and prepared as described hereinbelow. Aluminum chloride, chlorobenzene, chlorosulfonic acid, 2-chlorothiophene, dimenthylacetamide (DMAC), and fluorobenzene, and toluene were all supplied from Aldrich Chemical Company and used as received. 4,4′-Isopropylidenediphenol (Aldrich) (Bis A) was recrystallized from toluene and vacuum dried prior to use. Toluene (Aldrich) for the polymerizations was distilled over sodium metal prior to use.

EXAMPLE 2

Synthesis of 2-chloro-5-(sulfurylchloro)thiophene

Chlorosulfonic acid (1.72 moles), $CHCl_3$ (100 mL), and dry ice (to maintain the temperature between 0° and −10° C) were added to a 2000 mL beaker and stirred with a magnetic stirbar. Chlorothiophene (0.84 moles) was added dropwise over ten minutes, turning the mixture dark black. The solution was permitted to warm to room temperature and then was recooled to −10° C. with dry ice. The excess chlorosulfonic acid was quenched with ice water, and the organic layer was separated from the aqueous layer. The aqueous layer was extracted with methylene chloride, and the organic layers were combined, dried over $MgSO_4$, filtered, and concentrated in vacuo. Vacuum distillation (0.1 torr, 76°–80° C.) of the isolated oil yielded 93g (50%). $GCM_s$ (m/e):181 (100%, M—Cl), 183 (66%, (CM+2)—Cl), 216 (65%, M), 218 (45%, M+2).

EXAMPLE 3

Synthesis of 2-chloro-5-(4′-chlorophenylsulfonyl)thiophene Monomer

The synthesis of 2-chloro-5-(4′-chloropherylsulforyl) thiophene was carried out by the method illustrated in Scheme I.

Scheme I 2-chloro-5-(sulfurylchloro)thiophene (0.14 moles) prepared by the method of Example 2, chlorobenzene (1.3 moles), and aluminum chloride (0.14 moles) were added to a 300 mL, three-necked, round bottom flask topped with a reflux condensor. The black reaction mixture was stirred for two hours, at which time it was determined by gas chromatography that the reaction was complete. The reaction was quenched with water and the organic layer and aqueous layer were separated. The aqueous layer was extracted with methylene chloride and the organic layers were combined, dried over $MgSO_4$, filtered, and concentrated in vacuo to produce a solid. The solid was recrystallized thrice in methanol using carbon black initially to decolorize the hot methanol solution. The monomer produced was in quantitative yield of white crystals with a melting point of 108° C. and was greater than 99.9% pure.

EXAMPLE 4

Synthesis of 2-chloro-5-(4′-fluorophenylsulfonyl)thiophene Monomer

This monomer was synthesized as described in Example 3 for 2-chloro-5-(4′-chlorophenylsulfonyl) thiophene with 1.6 moles of fluorobenzene being substituted for chlorobenzene. The synthesis produced white crystals with a $T_m$=89.9° C.

EXAMPLE 5

Synthesis of Polymer of 2-chloro-5-(4′-chlorophenylsulfonyl)thiophene and Bisphenol A The polymerization of 2-chloro-5-(4′-chlorophenylsulfonyl) thiophene and BisA is presented in Scheme II.

Scheme II

Polymer synthesis was conducted in a three-necked, 100 mL, round bottom flask equipped with an overhead stirrer, a Dean-Stark trap, condensor, gas inlet, and thermometer. The flask was charged with 2-chloro-5-(4'-chlorophenylsulfonyl)thiophene (0.01364 moles), Bis A (0.01364 moles), dimethylacetamide (35 mL), potassium carbonate (0.04 moles, 3 eq.) and toluene (4 mL). This solution was heated to between 120°–125° C. and dehydrated via subsequent removal and addition of toluene over six hours. After dehydration, the solution was heated to 150° C. and maintained at this temperature for 18 hours to induce complete polymerization. The polymer was coagulated in a solution of 50% water and 50% methanol, dried, and reprecipitated from methylene chloride into methanol. The polymer was fractionally precipitated three times from tetrahydrofuran with water. The resulting polymer was determined by gel permeation chromatography to have a molecular weight of $M_n = 25000$.

This thiophene containing polymer showed similar properties to the phenyl-based poly(arylene ether sulfone)s. A solvent cast, vacuum-dried film of the polymer was of high quality and strength. This film was transparent, amber colored, and very creasable, with a $T_g = 160°$ C.

EXAMPLE 6

Figure 1:
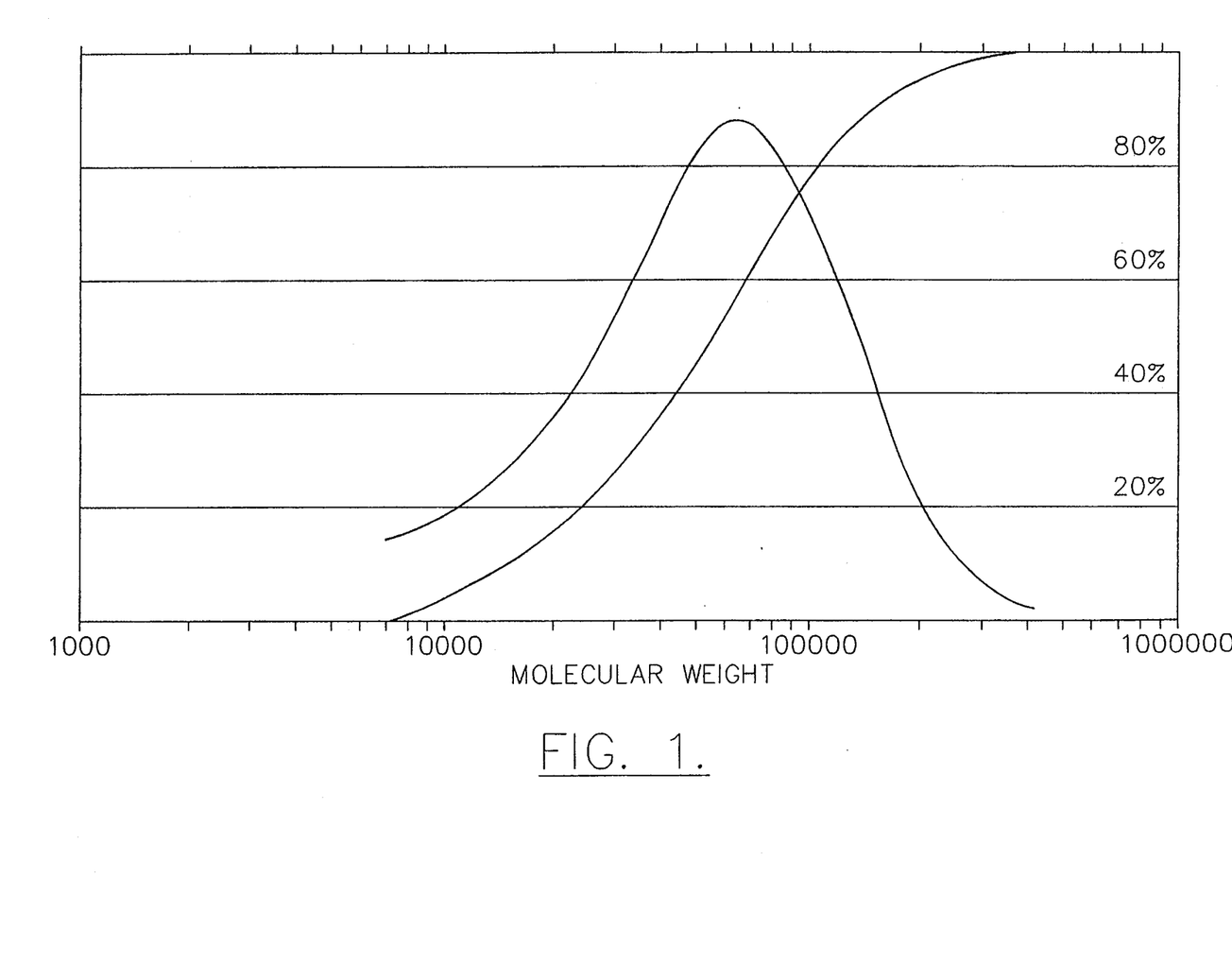
FIG. 1 is a gel permeation phase chromatogram indicating that the molecular weight of the thiophene-containing PAES of Example 6 is approximately 35,000.
Figure 2:
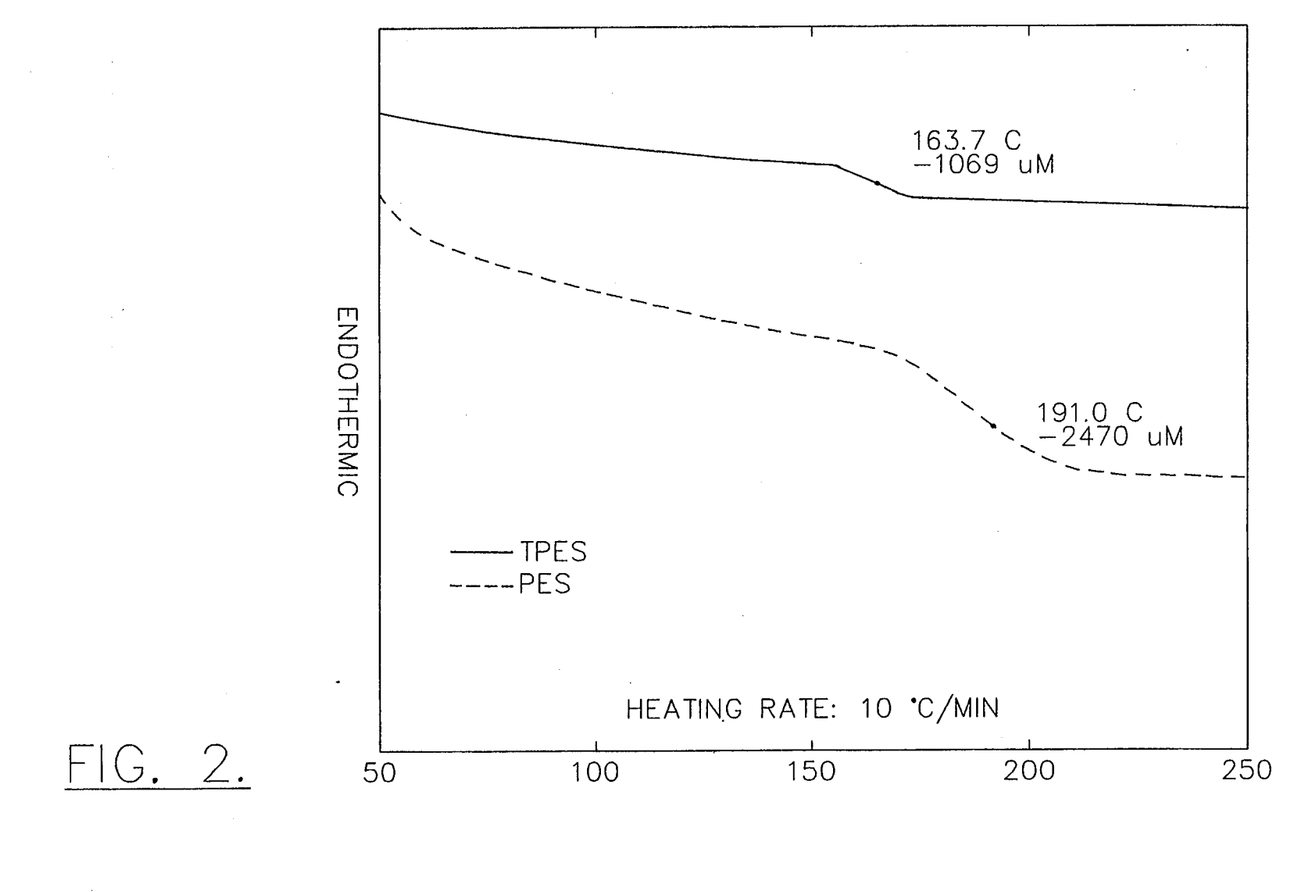
FIG. 2 is a differential scanning calorimetry (DSC) thermogram comparing the glass transition temperatures of conventional PES (191.0° C.) and the thiophene-containing PAES of Example 6 is (163.7° C.).
Figure 3:
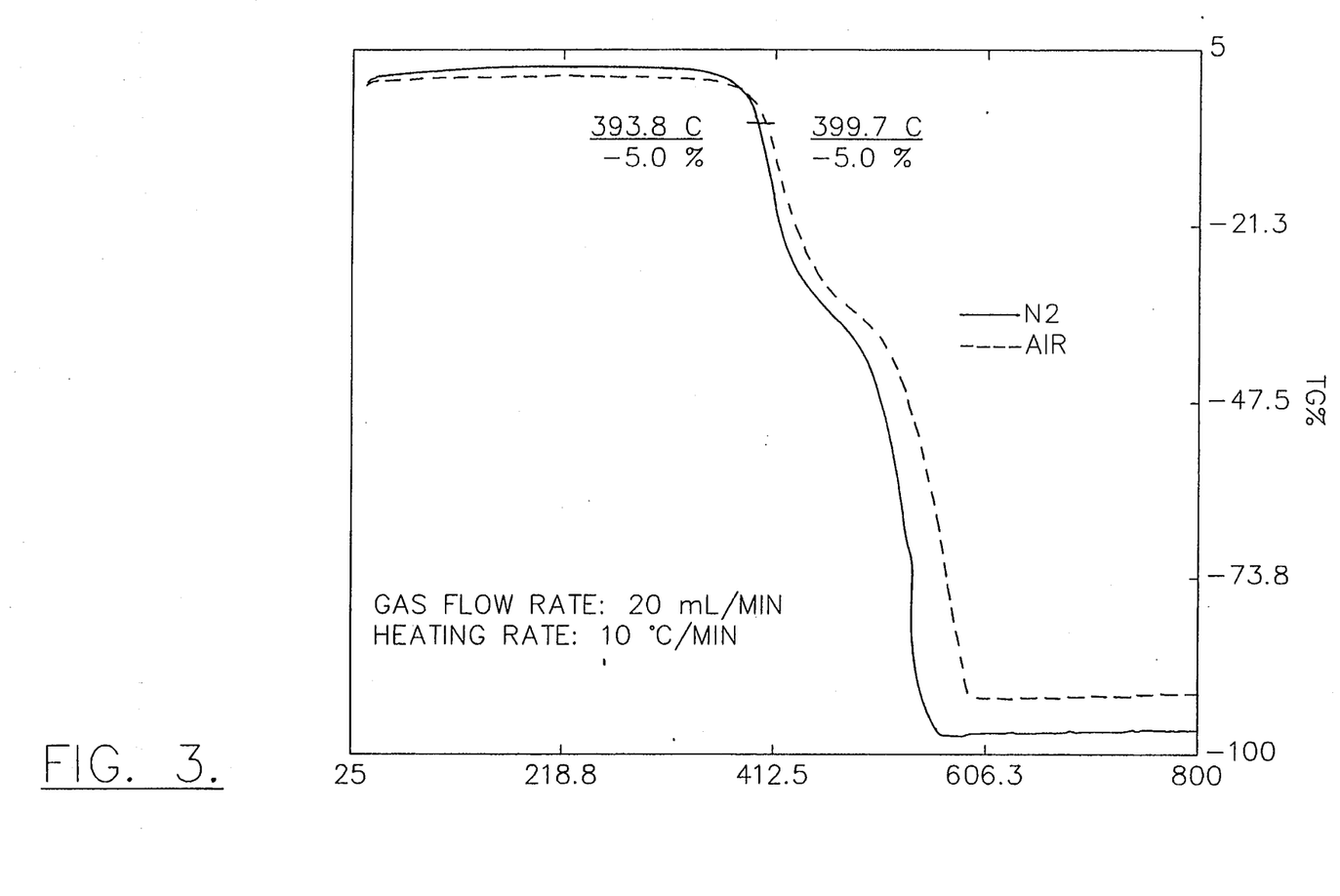
FIG. 3 is a thermal gravimetric analysis (TGA) thermogram of thiophene-containing PAES in air and in nitrogen.
Figure 4:
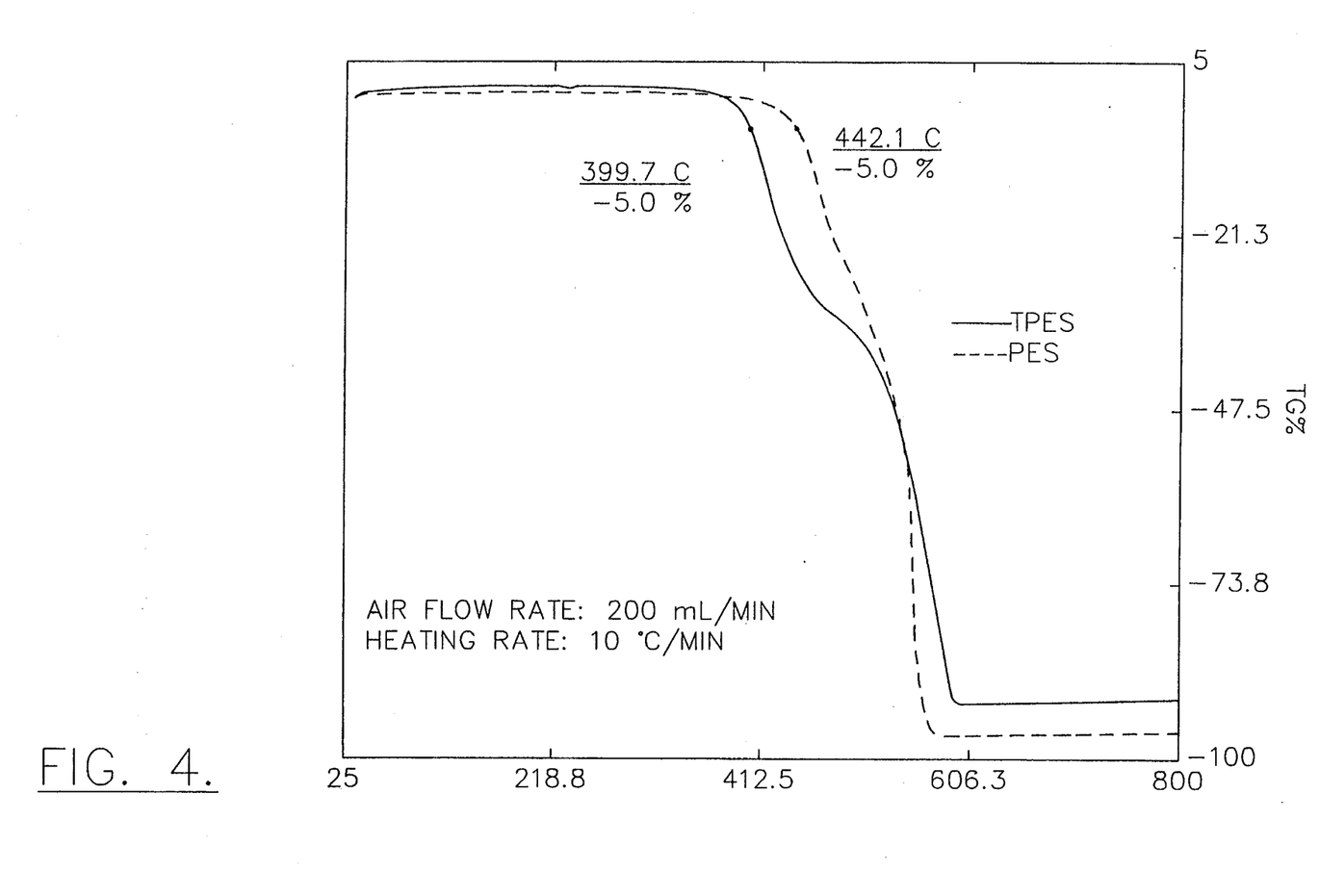
FIG. 4 is a TGA thermogram comparing weight loss of conventional PES and the thiophene-containing PAES of Example 6.

Synthesis of Polymer of 2-chloro-5-(4'-fluorophenylsulfonyl)thiophene and Bisphenol A This polymer was synthesized following the method described in Example 5, except that 2-chloro-5-(4'-fluorophenylsulfonyl)thiophene was substituted for 2-chloro-5-(4'-chlorophenylsulfonyl)thiophene. The synthesis produced a polymer with a molecular weight of $M_n = 35000$ (FIG. 1). The difference between the molecular weight of this polymer and the lower molecular weight of the polymer synthesized in Example 5 is attributed to the greater reactivity of the fluorine-based monomer versus the chlorine-based monomer. A solvent-cool, vacuum-dried film of the polymer was of high strength and quality. The film was of transparent amber hue and had a $T_g$ of 160° C. as determined by DSC (FIG. 2). TGA conducted on the polymer indicates 50% weight loss at approximately 399° C. in air and 393° C. in nitrogen (FIGS. 3 and 4).

EXAMPLE 7

Synthesis of 2-chloro-5-(4-hydroxyphenyl-sulfonyl)thiophene

The self-polymerizing monomer 2-chloro-5-[(4-hydroxyphenyl]sulfonyl)thiophene was prepared by each of the following synthetic methods.

A. 2-chloro-5-sulfurylchloro)thiophene was prepared as described in Example 2. 1 mol of this compound was added to an excess of aluminum chloride. A stoichiometric excess of anisole was added to the solution, and the reaction was allowed to proceed for 7 hours. The reaction is illustrated in Scheme 3.

Scheme 3

The ether linkage between the methyl group and position 4 of the phenyl moiety was then cleaved by acid hydrolysis. The product was recovered by recrystallization from ethanol and was produced in 45 percent yield.

B. 2-chloro-5-sulfurylchloro)thiophene was prepared as described in Example 2. 1 mol of this compound was mixed with ½ mol of diphenyl carbonate in FeCl₃ (15 wt %) and nitrobenzene, heated to 125° C., and allowed to react for 2 hours. The product, bis-4-(3'-chloro-2'-thiophenidyl-1-sulfonyl)phenyl anhydride, was recovered by recrystallization in ethanol in quantitative yield. The carbonate was then cleaved with base to form 2-chloro-5-(4-hydroxyphenylsulfonyl)thiophene. The process is illustrated in Scheme 4.

Scheme 4

The foregoing examples are illustrative of the present invention, and are not to be construed as limiting thereof. The invention is defined by the following claims, with equivalents of the claims to be included therein.

That which is claimed is:

1. A poly(arylene ether sulfone) comprising repeating units of Formula IV (IV)

wherein R is an aromatic moiety having at least one aromatic ring.

2. A poly(arylene ether sulfone) according to claim 1, wherein R comprises a moiety of Formula V

—A—O—B—   (V)

wherein A is an aromatic group having at least one aromatic ring, and wherein B is an aromatic moiety having at least one aromatic ring.

3. A poly(arylene ether sulfone) according to claim 2, wherein A comprises a moiety of the formula:

4. A poly(arylene ether sulfone) according to claim 2, wherein A comprises a moiety of the formula:

5. A poly(arylene ether sulfone) according to claim 3, wherein B comprises a moiety selected from the group consisting of:

and

6. A poly(arylene ether sulfone) according to claim 3, wherein B comprises a moiety of the formula:

7. A poly(arylene ether sulfone) according to claim 3, wherein B comprises a moiety of the formula:

8. A poly(arylene ether sulfone) according to claim 3, wherein B comprises a moiety of the formula:

9. A poly(arylene ether sulfone) according to claim 3, wherein B comprises a moiety of the formula:

10. A poly(arylene ether sulfone) according to claim 3, wherein B comprises a moiety of the formula:

11. A poly(arylene ether sulfone) according to claim 3, wherein B comprises a moiety of the formula:

12. A poly(arylene ether sulfone) according to claim 4, wherein B comprises a moiety selected from the group consisting of:

and

13. A poly(arylene ether sulfone) according to claim 4, wherein B comprises a moiety of the formula:

14. A poly(arylene ether sulfone) according to claim 4, wherein B comprises a moiety of the formula:

15. A poly(arylene ether sulfone) according to claim 4, wherein B comprises a moiety of the formula:

16. A poly(arylene ether sulfone) according to claim 4, wherein B comprises a moiety of the formula:

17. A poly(arylene ether sulfone) according to claim 4, wherein B comprises a moiety of the formula:

18. A poly(arylene ether sulfone) according to claim 4, wherein B comprises a moiety of the formula:

19. A poly(arylene ether sulfone) according to claim 4, wherein B comprises a moiety of the formula:

20. A polymeric film formed from a melt of a poly(arylene ether) sulfone according to claim 1.

21. A polymeric fiber formed from a melt of a poly(arylene ether) sulfone according to claim 1.

22. An article of manufacture formed from a poly(arylene ether)sulfone according to claim 1.

23. A composite according to claim 1, wherein said poly(arylene ether) sulfone comprises a matrix component of a composite material, and wherein said foreign substrate comprises an organic or inorganic filler.

* * * * *

UNITED STATES PATENT AND TRADEMARK OFFICE
CERTIFICATE OF CORRECTION

PATENT NO. : 5,410,013
DATED : April 25, 1995
INVENTOR(S) : Joseph M. DeSimone, Edward T. Samulski, Robert S. Archibald and Valeria V. Sheares It is certified that error appears in the above-indentified patent and that said Letters Patent is hereby corrected as shown below:

Column 1, Line 6, after "now abandoned." insert --This invention was made with government support under Grant No. N00014-92-J-1374 awarded by the Office of Naval Research. The government has certain rights in this invention.--

Signed and Sealed this

Ninth Day of April, 1996

Attest:

BRUCE LEHMAN

Attesting Officer        Commissioner of Patents and Trademarks